United States Patent [19]
Sie et al.

[11] Patent Number: 4,812,433
[45] Date of Patent: Mar. 14, 1989

[54] PROCESS FOR THE PRODUCTION OF METHANOL AND A COMPOSITION SUITABLE FOR USE AS A CATALYST IN SAID PROCESS

[75] Inventors: Swan T. Sie; Eit Drent; Willem W. Jager, all of Amsterdam, Netherlands

[73] Assignee: Shell Oil Company, Houston, Tex.

[21] Appl. No.: 175,026

[22] Filed: Mar. 30, 1988

[30] Foreign Application Priority Data

Apr. 3, 1987 [GB] United Kingdom ................ 8708005

[51] Int. Cl.$^4$ ........................ B01J 31/04; B01J 31/12; B01J 31/28
[52] U.S. Cl. .................................... 502/117; 518/717
[58] Field of Search ........................ 502/117; 518/717

[56] References Cited

U.S. PATENT DOCUMENTS 4,619,946 10/1986 Sapienza et al. ................ 518/717 X

FOREIGN PATENT DOCUMENTS 56169634 12/1981 Japan .

Primary Examiner—Patrick P. Garvin
Attorney, Agent, or Firm—Y. Grace Tsang

[57] ABSTRACT

A process for producing methanol which comprises the following consecutive steps:

Step 1: Preparing a novel catalytic system by combining (a) a nickel (b) a hydride of an alkali metal or of an alkaline earth metal, and (c) an ester of formic acid which originates from an external source, and allowing the combined components (a), (b) and (c) to react; and Step 2: Contacting a gaseous mixture of CO and $H_2$ with the catalytic system prepared in step 1.

15 Claims, No Drawings

PROCESS FOR THE PRODUCTION OF METHANOL AND A COMPOSITION SUITABLE FOR USE AS A CATALYST IN SAID PROCESS

FIELD OF THE INVENTION

The invention relates to a process for the production of methanol. The invention also relates to a novel catalyst composition useful for the production of methanol.

Background of the Invention

A process for the production of methanol is described in U.S. patent specification 4,619,946, issued Oct. 28, 1986. The patent concerns reacting carbon monoxide with hydrogen in the presence of a catalytic system of the type NaH-RONa- nickel acetate in which R represents an alkyl group having 1-6 carbon atoms. This catalytic system can be made more active by "conditioning", involving contacting for a prolonged time with a gaseous mixture comprising carbon monoxide and hydrogen at such an elevated temperature and elevated pressure that a substantial amount of carbon monoxide and hydrogen is consumed for this conditioning.

Another process for the production of methanol is described in Japanese patent application publication No. 56-169,634, published Dec. 26, 1981. The patent application concerns reacting carbon monoxide and hydrogen in the presence of a catalyst comprising a nickel compound and an alkali metal alkoxide.

It is an object of the present invention to produce methanol in the presence of a catalytic system having enhanced activity.

It is another object of the present invention to produce methanol in the presence of a catalytic system that retains its activity for a long time.

SUMMARY OF THE INVENTION

Accordingly, the invention provides a process for the production of methanol which process comprises the following consecutive steps:
Step 1:
Preparing a catalytic system by combining the following components:
Component (a): a nickel salt,
Component (b): a hydride of an alkali metal or of an alkaline earth metal, and
Component (c): an ester of formic acid which originates from an external source,
and allowing the combined components (a), (b) and (c) to react; and
Step 2:
Contacting a gaseous mixture comprising carbon monoxide and hydrogen with the catalytic system prepared in step 1.

DETAILED DESCRIPTION OF THE INVENTION

The anion of the salt in component (a) may be derived from a great variety of acids. Preference is given to a salt of an acid having a pKa, measured in aqueous solution at 25° C., of less than 4.70. It is preferred that the salt in component (a) is a salt of a carboxylic acid. Among these acids preference is given to formic acid and oxalic acid. Component (a) is most preferably nickel formate or nickel oxalate. Among these two salts, nickel formate is most preferred.

Examples of carboxylic acids from which component (a) may be derived are dicarboxylic acids such as malonic acid, dimethylmalonic acid, succinic acid, glutaric acid, adipic acid, pimelic acid, suberic acid, azelaic acid, phthalic acid, isophthalic acid and terephthalic acid. The carboxylic acids from which component (a) may be derived may contain substituents, for example, alkoxy groups particularly those having not more than five carbon atoms, hydroxy groups, cyano groups and fluorine, chlorine, bromine and iodine atoms. Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5-dichlorobenzoic acid, 3 5-dibromobenzoic acid, cyanoacetic acid, monofluoroacetic acid, difluoroacetic acid, trifluoroacetic acid and trichloroacetic acid.

Examples of other acids from which compoent (a) may be derived are hydrochloric acid, sulfuric acid, nitric acid and phosphoric acid.

A mixture of the salts in question may be used in component (a), for example, of a formate and an oxalate or of a formate and a benzoate.

The salts in component (a) may contain crystal water but are preferably free therefrom.

Component (b) may be a hydride of lithium, sodium, potassium, rubidium, cesium, calcium, strontium, barium or magnesium. Preference is given to a hydride of an alkali metal, particularly to sodium hydride and potassium hydride. The hydride may be added as such, but it has been found that the hydride may advantageously be added as a suspension in an inert diluent, for example, a mineral oil, such as a heavy hydrocarbon oil, preferably a so-called white paraffin oil.

If desired, an alcoholate of an alkali metal or an alcoholate of an alkaline earth metal may also be combined in the catalytic system. This alcoholate is preferably a sodium alcoholate or a potassium alcoholate. The alcoholate may be cycloaliphatic but is preferably aliphatic. Preference is given to alkanolates, in particular to those having in the range of from 1 to 20 carbon atoms per molecule. Among the latter alkanolates those having in the range of from 4 to 12 carbon atoms per molecule are preferred. Examples of such alkanolates are those of tert-butyl alcohol, tert-pentyl alcohol, hexanol, heptanol and alkanols having in the range of from 8 to 12 carbon atoms per molecule. Tert-butylates and tert-pentylates are particularly preferred. Alcoholates derived from dihydric alcohols may also be used, for example, those derived from ethylene glycol, propylene glycol, 1,3-dihydroxypropane, 1,2-butanediol, 1,3-butanediol, 1,4-butanediol, 2,3-butanediol or 1,2-pentanediol. The alcoholate may also be an alcoholate derived from glycerol. The alcoholate may be a mixture of alcoholates, for example, of a tert-butylate and an ethylene glycolate or of a tert-pentylate and a 1,4-butanediolate.

It has, moreover, been found that the yield of methanol can be further enhanced by preparing the alcoholate in component (b) in situ. This preferred embodiment of the present invention may conveniently be carried out by the reaction of an alcohol with a hydride of an alkali metal and/or a hydride of an alkaline earth metal.

The ester of formic acid originates from an external source; in other words, it has not been formed in situ. The ester of formic acid is suitably added to components (a) and (b) under an inert gas such as nitrogen or a noble gas, in a closed reactor, starting at about atmospheric pressure. The components (a), (b) and (c) are allowed to react for a period which is not critical and which may vary within wide ranges, for example, between 5 seconds and 5 hours and preferably between 1 minute and 1 hour. It is within the scope of the present invention to carry out step 1 in the presence of a small amount of added carbon monoxide, for example, an amount which is equivalent to a partial pressure thereof of less than 5 bar, preferably less than 1 bar. However, step 1 is preferably carried out in the absence of added carbon monoxide.

The ester of formic acid of component (c) may be derived from a cycloaliphatic alcohol or an aliphatic alcohol; the cycloaliphatic and aliphatic alcohols are preferably primary or secondary. The aliphatic alcohol preferably has not more than 12 carbon atoms per molecule and is preferably an alkanol. Methyl formate is most preferred because this ester can be in situ converted to the desired methanol. Other examples of formates are ethyl formate, propyl formate, isopropyl formate and butyl formate. The cycloaliphatic alcohols from which the formate may be derived preferably do not have more than 12 carbon atoms per molecule, cyclohexanol is an example thereof.

Step (1) of the process according to the present invention may be carried out at a temperature which is not critical and may vary within wide ranges. It is a feature of the present invention that step (1) can be carried out at relatively low temperature, preferably in the range of from 0° C. to 100° C. Very good results are usually obtained at temperatures in the range of from 30° C. to 60° C.

It has, furthermore, been found that step 2 of the process according to the present invention can be used for the simultaneous reaction of additional quantities of an ester of formic acid with hydrogen with formation of the alcohol from which the ester is derived. This can be effected by contacting an ester of formic acid originating from an external source with the catalytic system when being used in step 2. These additional quantities may be added during the whole duration of step 2 or during a part of the duration.

Step 2 of the process according to the present invention may be carried out at a temperature and a pressure which are not critical and may vary within wide ranges. Preferably, a temperature in the range of from 30° C. to 150° C. and a pressure in the range of from 5 to 100 bar are used.

The process according to the present invention may be carried out with an organic diluent in which the catalytic system is present, at least partly, as a suspension. Suitably, a weight ratio of organic diluent to component (a) in the range of from 0.1 to 5000 is used, but this weight ratio may be lower than 0.1 or higher than 5000. The process according to the present invention is preferably carried out using a molar ratio of component (c) to component (a) in the range of from 0.5:1 to 100:1 and, more preferably, from 1:1 to 50:1, but the use of molar ratios below 0.5 and above 100 is not excluded. The process may be carried out using a molar ratio of component (b) to component (a) which is not critical and may vary within wide ranges, preferably in the range of from 0.1 to 1 to 100 to 1.

Any inert diluent may in principle be used. Examples of suitable diluents are ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzene; halogenated alkanes, such as dichloromethane and carbontetrachloride; alkanes, such as hexane, heptane, octane, 2,2,3-trimethylpentane and kerosene fractions; cycloalkanes, such as cyclohexane and methylcyclohexane; sulfoxides, such as dimethyl sulfoxide; sulfones, such as diisopropyl sulfone, tetrahydrothiophene 1,1-dioxide (also referred to as "sulfolane"), 2-methyl-4-butylsulfolane and 3-methylsulfolane. Mixtures of two or more solvents may be used. Very good results have been obtained with ethers.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably in the range of from 1:0.2 to 1:20. The carbon monoxide and hydrogen may be obtained by partial oxidation of hydrocarbons, for example, of natural gas.

The methanol produced according to the invention may be used for a variety of purposes, for example, for the manufacture of synthetic gasoline, as a fuel component and for the production of methyl tert-butyl ether.

The process according to the present invention may be carried out batchwise, semi-continuously or continuously. It is preferred to remove methanol in the gaseous phase from the reaction mixture being formed in step 2. This can be done by stripping the reaction mixture with carbon monoxide and hydrogen. Methanol can be recovered from the used stripping gas in any suitable manner, for example, by condensation.

The invention also provides a novel composition prepared by combining the following components:
  Component (a): a nickel salt,
  Component (b): a hydride of an alkali metal or of an alkaline earth metal, and
  Component (c): an ester of formic acid which originates from an external source,
    and allowing the combined components (a), (b) and (c) to react.

The ester of formic acid may have been prepared in any suitable manner, for example, by carbonylation of methanol in the presence of a base.

Said novel composition may be used as a catalytic system in the process according to the present invention.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The invention is further illustrated by means of the following Examples. Each experiment was carried out in a 300 ml Hastelloy C autoclave ("Hastelloy" is a trade mark) provided with a magnetic stirrer. The sodium hydride was used as a suspension in white paraffin oil containing 80% by weight of NaH. The ethyl formate contained 6% by weight of formic acid, the methyl formate was pure. The reaction mixtures were analyzed by means of gas-liquid chromatography.

EXAMPLE 1

The autoclave was charged under a nitrogen atmosphere with diglyme (50 ml), nickel formate.$2H_2O$ (10 mmol), sodium hydride (60 mmol) and tert-butyl alcohol (20 mmol), heated to a temperature of 45° C. with stirring and kept at this temperature for 0.5 hour. Then, consecutively, a solution of tert-butyl alcohol (30 mmol) in diglyme (50 ml) and ethyl formate (2 ml, 23 mmol) were introduced into the autoclave and the autoclave was sealed. At this moment step 1 was terminated. Then, step 2 was started by admitting a mixture of 1 volume of carbon monoxide and 2 volumes of hydrogen until a pressure of 45 bar was obtained.

The autoclave was further heated to a temperature of 80° C. and the pressure was then kept at a value between 30 and 60 bar by introducing intermittently said mixture of carbon monoxide and hydrogen.

The pressure was still decreasing after 3 hours at 80° C. which indicates that the catalytic system had retained activity. At this moment the autoclave was allowed to adopt ambient temperature and when depressurized. The reaction mixture contained a yellow solid substance, 7.2 g of methanol, 1 g of ethanol and no ethyl formate, the ethanol originating from ethyl formate.

EXAMPLE 2

Example 1 was repeated with the difference that tert-butyl alcohol was replaced with tert-pentyl alcohol and that not 2 ml but 10 ml (115 mmol) of ethyl formate were used.

The reaction mixture contained a yellow solid substance, 7.5 g of methanol, 4.75 g of ethanol and no ethyl formate, the ethanol originating from ethyl formate.

EXAMPLE 3

Example 2 was repeated with the difference that nickel formate.$2H_2O$ (10 mmol) was replaced with nickel oxalate.$2H_2O$ (10 mmol).

The reaction mixture contained a yellow solid substance, 6.7 g of methanol, 4.5 g of ethanol, 1.2 g of methyl formate and 5.7 mmol of ethyl formate.

Comparison with Example 2 shows that the use of nickel formate gives a higher yield of methanol than the use of nickel oxalate.

EXAMPLE 4

Example 1 was repeated with the difference that tert-butyl alcohol was not used, that diglyme (50 ml) was replaced with diglyme (100 ml) and that not 2 ml but 10 ml of ethyl formate were used.

The pressure was still decreasing after 5 hours instead of 3 hours at 80° C. The reaction mixture contained at the end of this period a yellow solid substance, 5.5 g of methanol, 3.7 g of ethanol and 1.3 g of ethyl formate.

Comparison with Example 1 shows that the presence of tertbutyl alcohol is not necessary.

EXAMPLE 5

The autoclave was charged under a nitrogen atmosphere with diglyme (50 ml), nickel formate.$2H_2O$ (10 mmol), sodium hydride (60 mmol) and tert-pentyl alcohol (30 mmol), heated to a temperature of 45° C. with stirring and kept at this temperature for 30 minutes. Then, consecutively, a solution of tert-pentyl alcohol (30 mmol) in diglyme (50 ml) and methyl formate (10 ml) were introduced into the autoclave and the autoclave was sealed. At this moment step 1 was terminated.

Then, a mixture of 1 volume of carbon monoxide and 2 volumes of hydrogen was admitted until a pressure of 45 bar was obtained.

Then consecutively, the autoclave was further heated to a temperature of 80° C., after 0.5 hour hydrogen was admitted until the partial pressure thereof increased by a value of 30 bar, after 55 minutes hydrogen and carbon monoxide were admitted until the partial pressures thereof increased by a value of 24 bar and 8 bar, respectively, after 1.5 hours hydrogen and carbon monoxide were admitted until the partial pressure thereof increased by a value of 24 and 8 bar, respectively, and the contents of the autoclave were allowed to react for 1 hour. At the end of this period the autoclave was allowed to adopt ambient temperature and depressurized. The reaction mixture contained a yellow solid substance, 11.3 g of methanol and no methyl formate.

EXAMPLE 6

The experiment of Example 5 was repeated with the difference that nickel formate.$2H_2O$ (10 mmol) was replaced with nickel acetate.$4H_2O$ (10 mmol), that, after heating the autoclave to a temperature of 80° C., the autoclave was kept at this temperature for a period of 2 hours, then heated to a temperature of 100° C. and kept at this temperature for 3 hours.

At 80° C. no reaction was observed. The reaction mixture contained a yellow-green solid substance, 1.1 g of methanol and 4.5 g of methyl formate.

Comparison with Example 5 shows that the use of nickel formate.$2H_2O$ gives a higher yield of methanol than the use of nickel acetate.$4H_2O$.

Then, 20 minutes later, hydrogen was introduced into the autoclave to increase the partial pressure thereof by 20 bar, 40 minutes thereafter carbon monoxide was introduced to increase the partial pressure thereof by 6 bar and the contents of the autoclave were allowed to react for a further 1 hour.

The reaction mixture contained a yellow substance, 4.5 g of methanol and 0.4 g of methyl formate.

COMPARATIVE EXPERIMENT A

Step 1 of Example 5 was repeated with the difference that methyl formate (10 ml) was not used. Then, a mixture of 1 volume of carbon monoxide and 2 volumes of hydrogen was admitted until a pressure of 45 bar was obtained.

Then, the autoclave was further heated to a temperature of 80° C. and kept at this temperature for a period of 3 hours. A pressure drop of only 3 bar was observed at the end of this period. The reaction mixture contained less than 1 g of methanol.

COMPARATIVE EXPERIMENT B

The autoclave was charged under a nitrogen atmosphere with diglyme (50 ml), nickel formate.$2H_2O$ (10 mmol), tert-pentyl alcohol (20 mmol) and sodium hydride (60 mmol), heated to a temperature of 45° C. with stirring and kept at this temperature for 30 minutes. Then, consecutively, a solution of tert-pentyl alcohol (30 mmol) in diglyme (50 ml) and methanol (4 g) were introduced into the autoclave and the autoclave was sealed. A mixture of 1 volume of carbon monoxide and 2 volumes of hydrogen was admitted until a pressure of 45 bar was obtained. The autoclave was heated to a temperature of 80° C. and kept at this temperature for 3 hours under constant pressure of said gas mixture. At the end of this period the autoclave was allowed to adopt ambient temperature and depressurized.

The reaction mixture contained a yellow substance, 5.3 g of methanol and 3.2 g of methyl formate. Since 4 grams of methanol had been added to the autoclave, only 1.3 g of methanol had actually been produced.

Comparison with Example 5 shows that combining methyl formate in the catalytic system in step 1 considerably enhances the formation of methanol.

EXAMPLE 7

The autoclave was charged under a nitrogen atmosphere with diglyme (50 ml), nickel formate.$2H_2O$ (10 mmol), tert-pentyl alcohol (20 mmol) and sodium hydride (60 mmol), heated to a temperature of 45° C. with stirring and kept at this temperature for 30 minutes. Then, a solution of tert-pentyl alcohol (30 mmol) in diglyme (50 ml) was introduced and the autoclave was sealed.

Into the sealed autoclave 10 ml of methyl formate were pumped which resulted in an increase of the pressure to about 5 bar. At this moment step 1 was terminated.

Subsequently, the autoclave was further pressurized with 30 bar of hydrogen and with carbon monoxide until a pressure of 45 bar was obtained. The autoclave was then heated to a temperature of 80° C. Thirty minutes after attaining this temperature the autoclave was repressurized with 15 bar hydrogen until a pressure of 45 bar was obtained, 1 hour later, the autoclave was repressurized with 30 bar hydrogen until a pressure of 60 bar was obtained and 10 ml of methyl formate was pumped into the autoclave. The autoclave was repressurized 1.5 hours later with 5 bar of carbon monoxide and 1.5 hours later the autoclave was repressurized with 15 bar of hydrogen. The autoclave was allowed to adopt ambient temperature and depressurized 30 minutes thereafter.

The reaction mixture contained a yellow solid substance, 12.5 g of methanol and 9.4 g of methyl formate, indicating that about half of the added methyl formate had been converted.

COMPARATIVE EXPERIMENT C

The autoclave was charged under a nitrogen atmosphere with diglyme (50 ml), nickel formate.$2H_2O$ (10 mmol), tert-pentyl alcohol (20 mmol) and sodium hydride (60 mmol), heated to a temperature of 45° C. with stirring and kept at this temperature for 30 minutes. Then, a solution of tert-pentyl alcohol (30 mmol) in diglyme (50 ml) was introduced and the autoclave was sealed.

Subsequently, a mixture of 1 volume of carbon monoxide and 2 volumes of hydrogen was admitted until a pressure of 45 bar was obtained; at this pressure, methyl formate (10 ml) was pumped into the autoclave. Then, the autoclave was kept for 2 hours at 80° C. and subsequently for 3 hours at 100° C.

At the end of this period the pressure was 37 bar; the autoclave was allowed to adopt ambient temperature and depressurized.

The reaction mixture contained a yellow solid substance, 3.1 g of methanol and 5.4 g of methyl formate.

Comparison with Example 8 shows that introduction of methyl formate into the autoclave before contacting the catalytic system with carbon monoxide and hydrogen has enhanced the production of methanol.

EXAMPLE 8

The autoclave was charged under a nitrogen atmosphere with diglyme (50 ml), water-free nickel acetate (10 mmol), tert-pentyl alcohol (20 mmol) and sodium hydride (60 mmol), heated to a temperature of 45° C. with stirring and kept at this temperature for 30 minutes. Then, a solution of tert-pentyl alcohol (30 mmol) in diglyme (50 ml) was introduced and the autoclave was sealed.

Into the sealed autoclave 10 ml of methyl formate were pumped, which resulted in an increase of the pressure to 5 bar.

Then, the autoclave was further pressurized with 30 bar of hydrogen and with carbon monoxide until a pressure of 45 bar was obtained. The autoclave was then heated to a temperature of 80° C. Thirty minutes after attaining this temperature the autoclave was repressurized with 30 bar hydrogen until a pressure of 60 bar was obtained and 30 minutes later the autoclave was repressurized with 24 bar hydrogen and 8 bar carbon monoxide until a pressure of 60 bar was obtained. Four hours thereafter the autoclave was allowed to adopt ambient temperature and depressurized.

The reaction mixture contained a yellow solid substance, 10.6 g of methanol and 2.8 g of methyl formate.

EXAMPLE 9

Example 8 was repeated until the autoclave was heated to a temperature of 80° C. Thirty minutes after attaining this temperature the autoclave was repressurized with 30 bar hydrogen until a pressure of 60 bar was obtained, 20 minutes later the autoclave was repressurized with 24 bar hydrogen and 8 bar carbon monoxide until a pressure of 70 bar was obtained, 35 minutes later the autoclave was repressurized with 24 bar hydrogen and 8 bar carbon monoxide until a pressure of 70 bar was obtained, 25 minutes later the autoclave was repressurized with 24 bar hydrogen and 8 bar carbon monoxide until a pressure of 70 bar was obtained and 45 minutes later the autoclave was repressurized with 24 bar hydrogen and 8 bar carbon monoxide until a pressure of 70 bar was obtained. Then, the autoclave was allowed to adopt ambient temperature, at which temperature the pressure was 22 bar.

The reaction mixture contained a yellow solid substance, 16.5 g of methanol and no methyl formate.

What is claimed is:

1. A composition prepared by combining the following components:
    Component (a): a nickel salt,
    Component (b): a hydride selected from the group consisting of a hydride of an alkali metal, a hydride of an alkaline earth metal, and a mixture thereof, and
    component (c): an ester of formic acid which originates from an external source.

2. The composition as claimed in claim 1, in which the salt in component (a) is a salt of an acid having a pKa, measured in aqueous solution at 25° C., of less than 4.70.

3. The composition as claimed in claim 1, in which the salt in component (a) is a salt of a carboxylic acid.

4. The composition as claimed in claim 3, in which the salt in component (a) is nickel formate.

5. The composition as claimed in claim 3, in which the salt in component (a) is nickel oxalate.

6. The composition as claimed in claim 1, in which said composition further comprises an alcoholate selected from the group consisting of an alcoholate of an alkali metal, an alcoholate of an alkaline earth metal, and a mixture thereof.

7. The composition as claimed in claim 6, in which the alcoholate is an alkanolate.

8. The composition as claimed in claim 7, in which the alkanolate has in the range of from 4 to 12 carbon atoms per molecule.

9. The composition as claimed in claim 8, in which the alkanolate is selected from the group consisting of tert-butylate, tert-pentylate, and a mixture thereof.

10. The composition as claimed in claim 1, in which component (b) is selected from the group consisting of sodium hydride, potassium hydride, and a mixture thereof.

11. The composition as claimed in claim 1, in which component (c) is a formate of an alkanol.

12. The composition as claimed in claim 11, in which component (c) is a formate of an alkanol having in the range of from 1 to 5 carbon atoms per molecule.

13. The composition as claimed in claim 12, in which component (c) is methyl formate.

14. A catalytic composition, suitable for the conversion of carbon monoxide and hydrogen to methanol, prepared by combining (a) nickel formate, (b) a hydride selected from the group consisting of sodium hydride, potassium hydride, and a mixture thereof, and (c) methyl formate originated from an external source, and allowing (a), (b) and (c) to react at a temperature in the range of from about 30° C. to about 60° C.

15. The composition as claimed in claim 14, in which the composition further comprises an alkanolate formed during the preparation of the catalyst system by the reaction of an alcohol selected from the group consisting of tert-butyl alcohol, tert-pentyl alcohol and a mixture thereof with a hydride selected from the group consisting of sodium hydride, potassium hydride, and a mixture thereof.

* * * * *